United States Patent [19]

Fischer

[11] 4,181,636

[45] Jan. 1, 1980

[54] PROCESS FOR PRODUCING IMMUNOLOGICAL DIAGNOSTIC REAGENTS

[75] Inventor: Ernst A. Fischer, Munchenstein, Switzerland

[73] Assignee: Hoffmann-La Roche Inc., Nutley, N.J.

[21] Appl. No.: 941,344

[22] Filed: Sep. 11, 1978

[30] Foreign Application Priority Data

Sep. 19, 1977 [GB] United Kingdom ............... 38893/77

[51] Int. Cl.$^2$ ............................................. C08L 89/00
[52] U.S. Cl. ......................................... 260/8; 424/12; 435/7; 435/181
[58] Field of Search ............................... 260/8; 424/12

[56] References Cited

U.S. PATENT DOCUMENTS

| 3,236,732 | 2/1966 | Arquilla | 424/12 |
| 3,551,555 | 12/1970 | Schuurs | 424/12 |
| 3,857,931 | 12/1974 | Hager | 424/12 |
| 4,045,384 | 8/1977 | Dorman | 260/8 |
| 4,046,723 | 9/1977 | Dorman | 260/8 |
| 4,140,662 | 2/1979 | Reckel et al. | 260/8 |

*Primary Examiner*—Edward M. Woodberry
*Attorney, Agent, or Firm*—Jon S. Saxe; Bernard S. Leon; George W. Johnston

[57] ABSTRACT

A process is disclosed for producing an immunological dignostic reagent by mixing an immunologically inert carboxylated latex polymer substantially free from any contaminating amino compound with a water-soluble activating agent and adding an immunologically active material thereto.

21 Claims, No Drawings

PROCESS FOR PRODUCING IMMUNOLOGICAL DIAGNOSTIC REAGENTS

BACKGROUND OF THE INVENTION

This invention relates to the manufacture of immunological diagnostic reagents.

The diagnosis of pathological or other conditions in human beings and animals often is carried out using immunological principles for the detection of antibodies or antigens in the body fluids of living beings. An antigen is a foreign substance which can be applied to a living being to cause the formation of certain soluble substances which are known as antibodies.

In a living being, the antibodies react with the antigens to act as a line of defense against the invading foreign substance. The response of a living being to the presence of antibodies becomes the basis for techniques which are useful for diagnosing certain diseases.

Such immunological testing techniques are based upon the antigen-antibody reaction which usually manifests itself by the formation of an insoluble complex or agglutination. More particularly, the presence of an antigen or an antibody can be determined by contacting the corresponding antibody or the corresponding antigen with a body fluid of the living being (e.g., urine, blood serum or a specially treated blood extract). The presence or the absence of the antibody or the antigen in the body fluid of the living being is ascertained by the presence or absence of an insoluble antigen-antibody complex.

Because some complexes form very slowly and/or have very small particle sizes, it is necessary to couple larger particles called carriers to the antigen or antibody to enable one to visibly discern the presence of any resulting complex. Carboxylated latex polymers, in particular carboxylated styrene butadiene latexes, are very useful as carriers in immunological assay systems based on agglutination reactions such as described above.

As disclosed in German Patent Application No. 2,203,377 (U.S. Pat. No. 3,857,931), a conventional procedure for covalently coupling an immunologically active material (e.g., antigen and antibody) to a latex polymeric carrier involves mixing an immunologically active material with discrete particles of latex and thereafter treating the resulting mixture with an activating agent such as, for example, a water-soluble carbodiimide by which the active material becomes bound to the latex particles. In the first step of this prior art procedure, the immunologically active material is adsorbed to the latex particles. In the second step, a chemical activating agent (e.g., carbodiimide) is added to introduce covalent links between the latex and the adsorbed immunologically active material.

The above-described prior art procedure, however, has the disadvantage that exposed reactive groups on the surface of the immunologically active material are also activated by the activating agent. Intramolecular and intermolecular crosslinking and/or polymerization of the immunologically active material results and a portion of the very expensive immunologically active material becomes impaired and therefore ineffective in an immunological test. This is particularly disadvantageous when antibodies are coupled to the latex particles because any modification of active sites on the antibody greatly diminishes their capacity to bind with antigens.

The present invention concerns an improved method for chemically bonding immunologically active materials to an immunologically inert carboxylated latex polymer which avoids the aforementioned disadvantages of the prior art. In accordance with the present invention non-selective modification in the immunologically active material is substantially reduced and reagents with a high level of biological activity are obtained.

SUMMARY OF THE INVENTION

The present invention relates to a process for producing an immunological diagnostic reagent comprising a carboxylated latex polymer carrier having bound thereto an immunologically active material. In accordance with the process of the present invention, carboxylated latex polymer which is substantially free from any contaminating amino compounds is mixed with a water-soluble activating agent and an immunologically active material is added thereto. The immunologically active material becomes bound to the carboxylated latex polymer thereby forming the diagnostic reagent.

The reagents obtained by the present invention are useful in diagnostic tests.

DESCRIPTION OF THE INVENTION

The present invention relates to a process for the manufacture of a water-insoluble immunological diagnostic reagent having a specific gravity of about that of water. The diagnostic reagent comprises discrete particles of an immunologically inert carboxylated latex polymer having condensed thereto through an amide linkage a known immunologically active material.

According to the present invention, an immunologically inert carboxylated latex polymer which is substantially free from any contaminating amino compounds is mixed with a water-soluble activating agent and subsequently an immunologically active material is added thereto. The immunologically active material thus becomes bound to the immunologically inert carboxylated latex polymer thereby forming the diagnostic reagent.

In accordance with the present invention, suitable carboxylated latex polymers include latex polymers which are water-insoluble, have a particle size in the range of from about 0.01 microns to about 0.9 microns and have the approximate specific gravity of water. Additionally, the particles are inert with respect to immunological diagnostic tests. After coupling with the immunologically active material, the specific gravity of the resulting diagnostic reagent particles is about 1.0 (0.95 to 1.05) thus enabling them to remain permanently in aqueous suspension. They also must have sufficient surface charge density so that, when coupled to the immunologically active material, their repulsive forces are sufficient to prevent aggregation.

Many types of immunologically inert carboxylated latex polymers are suitable for use in this invention provided they meet the criteria set forth above. This invention comprehends the use of all such suitable carboxylated latex polymers.

Typical latex polymers which are suitable in the practice of the subject invention are those comprised of carboxyl-containing polymers and copolymers of the following general compositions: polystyrene; polyvinyl pyridine; styrene-butadiene copolymers; acrylonitrile-butadiene copolymers; vinyl acetate-acrylate ester copolymers; vinyl chloride-acrylate ester copolymers. The various techniques of emulsion polymerization and further reaction of latex polymers offer a wide variety of means to incorporate into the latex particle the surface carboxyl groups needed for coupling with the water-soluble carbodiimides. For example, surface carboxyl groups may be incorporated by adding to the monomer mixture a carboxyl-containing monomer such as, for example, acrylic acid, methacrylic acid, itaconic acid, aconitic acid, fumaric acid and maleic acid or by a further chemical reaction of the latex polymer or copolymer surface in the latex state such as, for example, by oxidation of surface hydroxyl end groups to carboxyl groups or by hydrolysis of surface acrylate or methacrylate ester groups to carboxyl groups. Suitable latexes may be prepared by a wide variety of conventional emulsion polymerization techniques such as, for example, batch emulsion polymerization in which all of the ingredients are added to the polymerization reactor before the reaction is initiated, seeded emulsion polymerization in which a seed latex is added to the polymerization mixture to control the number of particles; semi-continuous emulsion polymerization in which the monomer mixture as well as other ingredients such as, for example, emulsifier and initiator solution are added continuously or shotwise to the reaction mixture throughout the polymerization and continuous emulsion polymerization in which the ingredients are added to the reactor continuously and the latex is removed from the reactor continuously. One method particularly suitable for incorporating surface carboxyl groups is seeded emulsion polymerization in which a monomer mixture containing a carboxyl-containing monomer is polymerized on the surface of the seed latex particles.

Preferred latex polymers are carboxylated styrene butadienes, carboxylated polystyrenes, acrylic acid polymers, methacrylic acid polymers, acrylonitrile polymers, acrylonitrile butadiene styrenes, polyvinyl acetate acrylates, polyvinyl pyridines, vinyl chloride-acrylates and the like.

Carboxylated latex polymers suitable in the practice of the invention are available commercially, for example, as aqueous latex suspensions usually in concentrations of from about 40% to about 60% by weight. Examples of suitable commercially available latex polymers are Amsco Res 4150, Amsco Res 3011 (American Mineral Spirits Co.); Dow Latex 815, Dow Latex 620, Dow Latex 859, Dow CL 241 (The Dow Chemical Co.); Hycar 1512, Hycar 1571, Hycar 1877X8, Hycar 2600x120 (Goodrich Chemical Co.); Gelva 900, Lytron 612, Lytron 624 (Monsanto); Rhoplex LC40 3216, Amberlite Ultrafine (Rohm and Haas).

The term "immunologically active material" in the context of the present invention refers to components of physiological fluids, cell and tissue extracts for which an immunological counterreactant is available or can be produced. Typical immunologically active materials are primary amines, amino acids, peptides, proteins, lipoproteins, glycoproteins, sterines, steroids, lipoids, nucleic acids, enzymes, hormones, vitamins, polysaccharides and alcaloids.

Table I

I. Microorganisms
   Bacteria
     1. Gram-positive *cocci*
       Streptococci (*pyogenes, fecalis* and *viridans*)
       Staphylococci (*aureus* and *albus*)
       Pneumococci (*D. pneumoniae*)
     2. Gram-negative *cocci*
       Neisseria (*gonorrhoeae* and *meningitidis*)
     3. Gram-positive *aerobic bacilli*

Table I-continued

*Bacillus anthracis*
       *Corynebacterium diphtheriae*
       Erysipelothrix
       *Listeria monocytogenes*
     4. Gram-positive *anaerobic bacilli*
       Clostridia (*botulinum, perfringens, welchii* and *tetani*)
     5. Gram-negative *anaerobic bacilli*
       Bacteroides
     6. Gram-negative intestinal *bacilli*
       Escherichia
       Klebsiella
       Enterobacter
       Proteus
       Pseudomonas
       Salmonella
       Shigella
     7. Gram-negative nonintestinal *bacilli*
       Pasteurella (*pestis* and *tularensis*)
       *Hemophilus influenzae*
       Brucella (*melitensis, abortus* and *suis*)
       *Bordetella pertussis*
       Malleomyces
     8. Spirochetes
       *Treponema pallidum*
       Leptospira
       Borrelia
     9. Mycoplasma
    10. Mycobacteria
    11. Vibrio
    12. Actinomyces Protozoa
   1. Intestinal Protozoa
     Amebae
   2. Flagellates
     Trichomonas
     Leishmania
     Trypanosomes
     Toxoplasma
   3. Sporozoa
     Plasmodia (*vivax, falciparum, malariae* and *ovale*)
   4. Intestinal nematodes
     Pinworms
     Hookworms
     Whip worms
   5. Tissue nematodes
     Trichinella
     Filaria (*Wuchereia bancroftii*)
     Dracunculus
   6. Trematodes
     Schistosomes
     Intestinal flukes
     Tissue flukes
   7. Cestodes
     Tapeworms
   8. Toxoplasma (*T. gondii*)

Fungi
   1. Sporotrichum
   2. Cryptococcus
   3. Blastomyces
   4. Histoplasma
   5. Coccidiodes
   6. Candida Viruses and Rickettsia
   1. Rickettsia
   2. Viruses
     Canine hepatitis
     Shope papilloma
     Influenza A & B
     Fowl plaque
     Herpes simplex
     Adenoviruses
     Polyema
     Rous sarcoma
     Vaccinia
     Poliovirus
     Measles
     Canine distemper
     Leukemia

Table I-continued

|     |     |
| --- | --- |
|     | Mumps |
|     | Newcastle disease |
|     | Sendai |
|     | ECHO |
|     | Foot and mouth disease |
|     | Psittacosis |
|     | Rabies |
|     | Extromelia |
|     | Arbor viruses |
| II. | Tissue antigens including organ specific antigens |
|     | Polysaccharides |
|     | Hyaluronidase |
|     | Tetanus toxin |
|     | Egg ovalbumin |
|     | Ovine serum albumin |
|     | Kidney |
|     | Liver |
|     | Skin |
|     | Heart (Myoglobin) |
|     | Gastrointestinal tract |
|     | Prostate |
|     | Embryonic antigens (alpha 1 fetoprotein) |
|     | Tumor antigens (carcinoembryonic antigen) |
|     | Muscle |
|     | Collagen |
|     | Amyloid |
| III. | Hormones |
|     | Pituitary hormones |
|     | Insulin |
|     | Glucagon |
|     | Thyroid hormone |
|     | Chorionic gonatropin |
|     | Chorionic growth hormone - prolactin |
|     | Human placental lactogen |
| IV. | Enzymes |
|     | Pancreatic chymotrypsinogen |
|     | Procarboxypeptidase |
|     | Deoxyribonculease |
|     | Ribonculease |
|     | Glyceraldehyde -3-phosphate dehydrogenase |
|     | Catalase |
|     | Peroxidase |
| V. | Blood Cell Antigens, Blood Group Substances and other |
|     | Isoantigens |
|     | Platelets |
|     | Megakaryocytes |
|     | Leuococytes |
|     | Erythrocytes |
|     | Blood group substances |
|     | Forsssman antigen |
|     | Histocompatibility antigens |
| VI. | Plasma Proteins |
|     | Fibrin and fibrinogen |
|     | Plasminogen and plasmin |
|     | Albumin |
|     | Immunoglobulins |
|     | α-1-antichymotrypsin |
|     | α-1-antitrypsin |
|     | Complement factors |
|     | Ceruloplasmin |
|     | Gc-globulin |
|     | Haptoglobin |
|     | α-2-macroglobulin |
|     | β-2-microglobulin |
|     | Orosomucoid |
|     | Prealbumin |
|     | Transferrin |
| VII. | Milk Proteins |
|     | Lactoferrin |
|     | Lysozyme |
|     | Secretory IgA |
|     | Secretory IgM |
|     | Secretory component |
| VIII. | Saliva Proteins |
|     | Secretory IgA |
|     | Secretory IgM |
|     | Secretory component |
| IX. | Urine Proteins |
| X. | Pathologic Proteins |
|     | Myeloma protein |
|     | Macroglobulinaemic proteins |
|     | Dysglobulinaemic proteins |
|     | Bence Jones I, II proteins |
|     | C-reactive protein |
|     | Cryoglobulins |
| XI. | Antibodies including autoantibodies |
|     | Antinuclear factor |
|     | Thyroid autoantibodies |
|     | Anti-Tamm-Horsfall protein |
|     | Cold agglutinins |
|     | Rheumatoid factor |
|     | Adrenal autoantibodies |
|     | Autoantibody to gastric parietal cells |
|     | in pernicious anemia |
|     | Anti-colon |
|     | Anti-liver |
|     | Anti-kidney |
|     | Autoantibodies to spermatozoa |
|     | Anti-heart |
|     | Muscle autoantibodies in myasthenia gravis |
|     | Autoantibodies to nervous tissue |
|     | Autoantibodies against fibrous tissue |
|     | and vascular components |
|     | Autoantibodies against platelets and megakaryocytes |
|     | Antibodies against trophoblasts |
|     | Antibodies to microorganisms |
|     | Antibodies to animal antigens |
|     | Antibodies to drugs |

Particularly preferred immunologically active materials are HPL (Human placental lactogen), albumin, choriongonadotropin, denatured gammaglobulin, antibodies against Albumin, IgA, IgG or IgM.

As used herein, an activating agent is a compound capable of converting the carboxyl groups on the latex polymer into COOR moieties wherein R represents a group with electron withdrawing properties. For example, the activating agent can be a water-soluble carbodiimide, Woodwards reagent K, i.e., N-ethyl-5-phenyl-isoxazolium-3'-sulfonate), a water-soluble chloroformate and the like.

Preferred activating agents in accordance with the invention are water soluble carbodiimides represented by the formula:

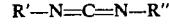

wherein R' and R" each are cyclo-lower alkyl, alkyl containing from 1 to 12 carbon atoms, aryl substituted lower alkyl, aryl, heterocyclic radicals, heterocyclic-substituted lower alkyl and di-lower alkyl amino; and acid addition and quaternary amine salts thereof.

The term "alkyl" as used herein denotes straight- and branched-chain alkyl groups containing from 1 to 20 carbon atoms. The term "lower alkyl" designates straight- and branched-chain lower alkyl groups containing from 1 to 7 carbon atoms. The term "cyclo-lower alkyl" designates saturated cyclic hydrocarbon radicals containing from 3 to 7 carbon atoms such as cyclohexyl, cycloheptyl, and the like. etc. The term "aryl" signifies mononuclear aromatic hydrocarbon radicals such as phenyl and polynuclear aromatic hydrocarbon radicals such as naphthyl. The term "aryl"

also signifies heteroaromatic groups which contain a 4 to 7 membered ring and which have in addition to carbon and hydrogen atoms 1 or 2 hetero atoms selected from the group consisting of nitrogen and oxygen. Among the heteroaromatic moieties are azepinyl, pyridyl, furyl, pyrrolyl, oxazolyl and imidazolyl. The term "heterocyclic radicals" denotes heterocyclic non-aromatic groups having a 5 to 7 membered saturated ring which contains from 1 to 2 hetero atoms selected from the group consisting of oxygen, nitrogen and mixtures thereof. Among the preferred heterocyclic ring radicals are morpholinyl, piperidinyl, tetrahydrofuryl, tetrahydropyranyl and pyrrolidinyl. Both the terms aryl and heterocyclic radicals can be unsubstituted as well as substituted in the 1, 2 or 3 position with a lower alkyl.

Illustratively, R' and R" each are cycloalkyl having from 5 to 6 carbon atoms in the ring, e.g., cyclopentyl and cyclohexyl; alkyl of from 1 to 12 carbon atoms, e.g., ethyl, n-propyl, isopropyl, n-butyl, sec.-butyl, iso-butyl, tert.-butyl, amyl, hexyl, heptyl, octyl, nonyl, decyl, undecyl and dodecyl; monoaryl substituted lower alkyl, e.g., benzylalpha- and beta-phenylethyl; monoaryl, e.g., phenyl; morpholino; piperidyl; morpholinyl substituted lower alkyl, e.g., ethyl morpholinyl; piperidyl substituted lower alkyl, e.g., ethyl piperidyl; di-lower alkyl-amino; pyridyl substituted lower alkyl, e.g., alpha, beta, gamma methyl or ethyl pyridyl; acid addition salts; and quaternary amines thereof.

According to a preferred process for producing diagnostic reagents by the present invention, discrete particles of a carboxylated latex polymer are procured and pretreated to remove any contaminating amino compounds, particularly compounds containing ammonium ions. Such compounds become associated with the oppositely charged carboxyl group on the latex polymers, for example, during the polymerization reaction. Any conventional method for treating a carboxylated latex polymer to substantially free the polymer from such amino compounds may be employed. For example, the carboxylated latex polymer can be washed several times with water and then treated with an ion exchange resin which replaces any ammonium ions present on the latex polymer with non-interfering cations such as sodium or potassium. Any conventional cationic ion exchange resins can be employed. Typical ions exchange resins include Dowex AG 50-X8, 200-400 mesh (styrene divinyl benzene polymer latice carrying nuclear sulfonic acid groups) and related resins like Rhom and Haas Amberlites, Diamond Shamrock Duolites, Permutite Company Zeocarbs and Nalco Chem. Co. Nalcites of same or similar composition.

The pretreated carboxylated latex polymer which is substantially free from any contaminating amino compound is mixed with a water soluble activating agent to chemically activate the latex polymer. The immunologically active material then is coupled to the carboxylated latex via activated esters. That is, the activating agent converts the carboxyl groups on the latex polymer into COOR moieties wherein R represents a group with electron withdrawing properties.

The pretreated latex polymer and the activating agent are reacted in an aqueous medium, preferably at room temperature (about 20° C. to about 25° C.) to activate the latex polymer. Temperatures from about 5° C. to about 40° C., however, are suitable for the reaction. The amount of activating agent can vary within broad limits and generally depends upon the density of the carboxyl groups on the latex polymer and upon the presence of additional negatively charged groups like sulfonate groups on the surface of the latexes. Generally, about 0.005 percent to about 6.0 percent by weight of a water-soluble activating agent, based on the weight of the particles, is suitable. However, about 0.05 to 2.0 percent by weight is preferably used.

The pH of the reaction of the latex polymer and activating agent preferably should be between about 2 and about 7. A pH between about 4 and about 5 is particularly preferred. To maintain the pH between these limits during the reaction, the pH of the latex suspension is preferably preadjusted between about 4 and about 5 with a suitable buffer.

The activated latex is then reacted with an immunologically active material to form a diagnostic reagent. Preferably, the reaction is performed at room temperature (about 20° C. to about 25° C.). Temperatures from about 0° C. to about 40° C., however, are also suitable.

The pH of the reaction between the activated latex and the immunologically active material is important since it should not be such as to denature said materials which are proteinaceous. Preferably, a pH of from about 5 to about 9.5 is maintained throughout the reaction by the use of appropriate buffer systems such as borate or phosphate buffers or the like.

The amount of immunologically active material linked to the immunologically inert latex polymeric carriers usually varies from about 0.01% to 15.0% by weight. However, each immunologically active material is utilized in an amount in which it is most successfully employed in a diagnostic test. Each material therefore is combined with the latex polymer carrier in a ratio suitable for the specific diagnostic requirements. The present invention comprehends within its scope the use of an amount of immunologically active material in combination with an immunologically inert, carboxylated latex polymeric carrier sufficient to provide a diagnostically effective reagent.

The resulting product can be utilized in specific diagnostic tests based upon recognized immunological principles. It can be used in any convenient concentration depending on the specific test, however, concentrations of from about 0.5% to about 2.5% by weight are suitable and a concentration of about 1.0% by weight is preferred.

The diagnostic reagents obtained by the present invention can be used for the determination of immunologically active materials in a direct or in an indirect (inhibition) agglutination test or in a kinetic photometric method such as, for example, is disclosed in German Patent Application No. 2,749,956 (U.S. Patent Application Ser. No. 849,926, filed Nov. 9, 1977, now abandoned).

In the direct test, the sample and the latex particles coated with the counterreagent for the immunologically active material to be determined are mixed and the agglutination observed visually or photometrically. The test is positive in case an agglutination takes place.

In the indirect test the sample is mixed with the counterreagent such as antiserum for the material to be determined and then with latex particles coated with the same material. The agglutination is observed visually or photometrically. The test is positive in case no agglutination occurs.

The reagent materials obtained with the method of the present invention can conveniently be packaged for commercial purposes (e.g., in a diagnostic reagent kit).

The following examples illustrate the invention. Unless otherwise indicated, temperatures are in degrees Celsius and percentages are expressed in weight per volume. Ratios (e.g., 1:1) denote parts by volume. In the examples, DOW Cl 241 connotes a polymer consisting of styrene, butadiene and a copolymerized carboxylic acid and is manufactured by Dow Chemical Co. Dowex AG 50-X8, 200-400 mesh, is a styrene divinyl benzene polymer latice carrying nuclear sulfonic acid groups, also manufactured by Dow Chemical Co., and marketed by Bio Rad Laboratories.

EXAMPLE 1

Pretreatment of latex polymer and coupling of bovine serum albumin (BSA)

125 ml of a commercial suspension of Dow CL 241 (carboxylated styrene butadiene copolymer; about 50% solids) was mixed with 375 ml of water and stirred for ½ hour on a magnetic stirrer. It was then centrifuged for 60 minutes at about 50,000×g. The residue was resuspended in 500 ml H$_2$O and recentrifuged three times. It was then taken up in water and its solid content adjusted to 8%. 100 ml of said 8% latex-suspension was treated 5 times with 10 g of wet Dowex AG 50-X8 200-400 mesh, (styrene divinyl benzene polymer latice carrying nuclear sulfonic acid group), which had been cycled and converted to the sodium form. Everytime the pH of the suspension was adjusted to 4.75.

With rapid stirring a solution of 10 mg 1-cyclohexyl-3-[2-morpholinyl-(4)-ethyl]-carbodiimide metho-p-toluenesulfonate (CMC) in 2 ml of water was added to 6 ml ionexchanged latex DOW CL 241 (78 mg/ml) adjusted to pH 4.75. After three minutes, 2 ml of a 1% bovine serum albumin solution was added. After the addition of the protein the pH of the suspension was 5.7. The mixture was kept stirring at room temperature for about 12 hours. During this time the pH shifted to 6.75. The latex was then centrifuged for 40 minutes at 44,000×g. The supernatant was discarded, the pellet suspended in water (total of about 40 ml), homogenized with a mixer and recentrifuged. The washing was repeated four times with 0.1 M borate buffer pH 8.5. After washing twice with distilled water, the latex was taken up in 20 ml distilled water. It was stabilized by adding 40 μl 20% sodium azide solution.

Slidetest

20 μl of rabbit anti BSA serum, diluted 1:400 in phosphate buffered saline (PBS) are mixed with 60 ml of the same buffer and 20 μl of the above BSA-latex suspension: Agglutination becomes visible after about 35 seconds.

This agglutination can be specifically inhibited by mixing 20 μl antiserum (1:400 in PBS) first with 30 μl of PBS and 30 μl of the same buffer containing 3 μg BSA. No sign of agglutination is detected for more than 4 minutes.

EXAMPLE 2

Coupling of sheep antihuman IgG antibodies to latex polymer 2.5 ml of a solution of 5.8 mg per ml sheep anti human IgG antibodies in 1:1 with water diluted phosphate buffered saline were dialyzed for two hours against 1 liter 0.015 M borate buffer pH 8.5. The slight precipitate was filtered off and activated latex, obtained as in example 1, with 2.5 mg CMC in place in 10 mg CMC, was added to the filtrate. The suspension was stirred at 4° C. overnight, centrifuged and washed 3× with 0.015 M borate buffer. It was finally taken up in 20 ml of borate buffer and stabilized through addition of 40 μl of a 20% sodium azide solution.

Slidetest

20 μl of the above sheep antihuman IgG-latex suspension was mixed with 60 μl veronal buffered saline (3.13 mM barbital 1.82 mM sodium barbital, 0.15 M sodium chloride, pH 7.5) containing 0.3 μg human IgG. Specific agglutination occurs within 30 seconds.

EXAMPLE 3

Coupling of human placental lactogen (HPL) to latex polymer 3 ml ionexchanged latex Dow CL 241 (77.6 mg/ml) was adjusted to pH 4.75. With rapid stirring a solution of 5 mg CMC in 1 ml of water was added to the suspension. After three minutes 1 ml of a 1% human placental lactogen solution was added. The mixture was kept stirring at room temperature overnight and then centrifuged for 40 min. at 45000×g. The latex was washed twice with 0.015 M borate buffer pH 8.5, then twice with 0.1 M borate buffer of the same pH. After washing twice with distilled water the latex was taken up in 10 ml of distilled water and stabilized by addition of 20 μl 20% sodium azide solution.

Slidetest

20 μl rabbit anti HPL serum diluted 1:20 with PBS are mixed with 60 μl of the same buffer and 20 μl of the above HPL-latex suspension. Agglutination occurs within 5 and 10 seconds.

This agglutination can be specifically inhibited by mixing 20 μl antiserum (1:20 in PBS) first with 30 μl of PBS and 30 μl of the same buffer containing 3 μg HPL. No agglutination at all is observable for more than a minute.

I claim:

1. A process for producing a water-insoluble immunological diagnostic reagent comprising:
   (a) providing an immunologically inert carboxylated latex polymer which is substantially free from any contaminating amino compounds;
   (b) mixing said immunologically inert carboxylated latex polymer with a water-soluble activating agent; and
   (c) adding an immunologically active material thereto to link the immunologically active material with the immunological inert carboxylated latex polymer, and thereby form the diagnostic reagent.

2. The process of claim 1 wherein step (a) comprises:
   (a) procuring an immunologically inert carboxylated latex polymer; and
   (b) pretreating said latex polymer to remove any amino compounds.

3. The process of claim 2 wherein the latex polymer is pretreated by:
   (a) washing said latex polymer with water; and
   (b) treating the washed latex polymer with a cationic ion exchange resin.

4. The process of claim 1 or 3 wherein the concentration of the water-soluble activating agent is about 0.005% to about 6% by weight.

5. The process of claim 1 or 3 wherein the water-soluble activating agent is a water-soluble carbodiimide.

6. The process of claim 5 wherein the water-soluble carbodiimide is 1-cyclohexyl-3-[2-morpholinyl-(4)-ethyl]-carbodiimide metho-p-toluenesulfonate.

7. The process of claim 1 or 3 wherein the immunologically inert carboxylated latex polymer approximately has the specific gravity of water and a particle size of about 0.01 to about 0.9 microns.

8. The process of claim 1 or 3 wherein the immunologically active material is linked to the immunologically inert latex polymer in an amount of about 0.01% to about 15.0% by weight.

9. The process of claim 1 or 3 wherein the immunologically inert carboxylated latex polymer is a water-insoluble carboxylated styrene butadiene copolymer.

10. The process of claim 1 or 3 wherein the immunologically active material is human chorionic gonadotropin.

11. The process of claim 1 or 3 wherein the immunologically active material is human albumin.

12. The process of claim 1 or 3 wherein the immunologically active material is denatured gamma globulin.

13. The process of claim 1 or 3 wherein the immunologically active material is human placental lactogen.

14. The process of claim 1 or 3 wherein the immunologically active material is an antibody against albumin.

15. The process of claim 1 or 3 wherein the immunologically active material is an antibody against IgA.

16. The process of claim 1 or 3 wherein the immunologically active material is an antibody against IgG.

17. The process of claim 1 or 3 wherein the immunologically active material is an antibody against IgM.

18. A process for manufacturing a water-insoluble immunological diagnostic reagent approximately having the specific gravity of water comprising:
    (a) providing discrete particles of carboxylated latex polymer which are immunologically inert;
    (b) pretreating said latex polymer to remove any amino compounds therefrom;
    (c) providing an activating agent which is water soluble;
    (d) mixing said pretreated latex polymer with said activating agent to activate the pretreated latex polymer; and
    (e) adding immunologically active material to the activated latex polymer to link the activated latex polymer to the active material by an amide link and thereby form the diagnostic reagent.

19. The process of claim 18 wherein the latex polymer is pretreated by:
    (a) washing the latex polymer with water; and
    (b) treating the washed latex polymer with a cationic ion exchange resin.

20. The process of claim 19 wherein the water-soluble activating agent is a water-soluble carbodiimide.

21. The process of claim 19 or 20 wherein the carboxylated latex polymer is a water-insoluble carboxylated styrene butadiene copolymer.

* * * * *